United States Patent [19]

Lachhein

[11] Patent Number: 5,159,086
[45] Date of Patent: Oct. 27, 1992

[54] PROCESS FOR THE PREPARATION OF PYRAZOLECARBOXYLIC ACID DERIVATIVES

[75] Inventor: Stephen Lachhein, Hofheim am Taunus, Fed. Rep. of Germany

[73] Assignee: Hoechst Aktiengesellschaft, Frankfurt am Main, Fed. Rep. of Germany

[21] Appl. No.: 643,449

[22] Filed: Jan. 18, 1991

[30] Foreign Application Priority Data

Jan. 20, 1990 [DE] Fed. Rep. of Germany ....... 4001600

[51] Int. Cl.$^5$ .......................................... C07D 231/14
[52] U.S. Cl. .............................. 548/374.1; 548/365.1; 548/375.1
[58] Field of Search ........................................ 548/378

[56] References Cited

U.S. PATENT DOCUMENTS 5,103,017 4/1992 Sohn et al. ........................... 548/378

*Primary Examiner*—Robert W. Ramsuer
*Attorney, Agent, or Firm*—Curtis, Morris & Safford

[57] ABSTRACT

Process for the preparation of pyrazolecarboxylic acid derivatives of the formula I

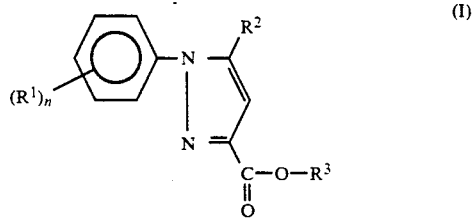

in which
$R^1$ independently of one another is haloalkyl or halogen,
$R^2$ is alkyl or alkynyl,
$R^3$ is an alkali metal or alkaline earth metal, hydrogen, alkyl or alkoxyalkyl and
n=1 or 2, by reaction of a compound of the formula II

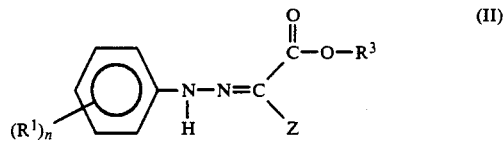

in which
Z is chlorine or bromine, with an enol ether of the formula III

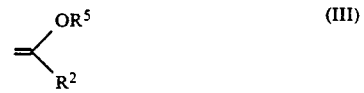

in which
$R^5$ is alkyl, to give a compound of the formula IV

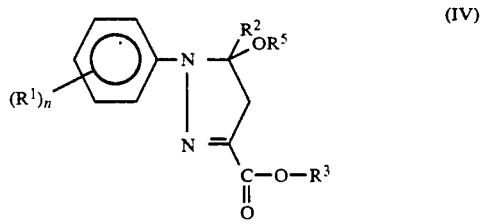

and its subsequent aromatization to give the compound I, wherein the reaction of the compound II with the compound III to give the compound IV is carried out in a 2-phase system (aqueous/organic) in the presence of an inorganic base at temperatures of 40°–100° C. and at pH values of 7–10 and then the compound IV formed is aromatized, without prior isolation, under acidic conditions in a 2-phase system (aqueous/organic) to give the compound of the formula I.

6 Claims, No Drawings

PROCESS FOR THE PREPARATION OF PYRAZOLECARBOXYLIC ACID DERIVATIVES

The present invention relates to a process for the preparation of pyrazolecarboxylic acid derivatives of the formula I

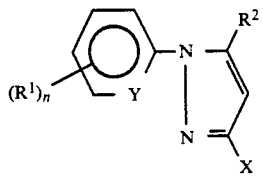

in which
Y is C—H or N,
$R^1$ independently of one another is ($C_1$–$C_4$)-alkyl, ($C_1$–$C_4$)-haloalkyl, ($C_1$–$C_4$)-alkoxy, ($C_1$–$C_4$)-haloalkoxy or halogen,
$R^2$ is ($C_1$–$C_{12}$)-alkyl, ($C_3$–$C_7$)-cycloalkyl, ($C_2$–$C_8$)-alkenyl or ($C_2$–$C_4$)-alkynyl,
X is $COOR^3$, $CON(R^4)_2$, $COSR^3$, CN or

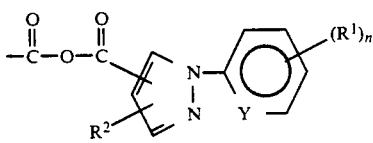

$R^3$ is an alkali metal or alkaline earth metal, hydrogen, ($C_1$–$C_{10}$)-alkyl, ($C_3$–$C_{20}$)-alkenyl, ($C_3$–$C_{10}$)-alkynyl, ($C_3$–$C_7$)-cycloalkyl, phenyl($C_1$–$C_4$)-alkyl, where phenyl can be substituted by halogen, tris-($C_1$–$C_4$)-alkylsilyl-($C_1$–$C_4$)-alkyl or ($C_1$–$C_4$)-alkoxy-($C_1$–$C_4$)-alkyl, independently of one another is H, ($C_1$–$C_{10}$)-alkyl, ($C_3$–$C_7$)-cycloalkyl which can be substituted, or 2 radicals $R^4$, together with the nitrogen atom linking them, form a 4- to 7-membered heterocyclic ring and
n is 1 to 3, by reaction of a compound of the formula II

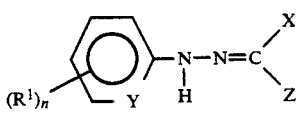

in which
$R^1$, X, Y and n have the abovementioned meanings and
Z is chlorine or bromine, with an enol ether of the formula III

in which $R^2$ has the abovementioned meaning and
$R^5$ is ($C_1$–$C_6$)-alkyl, X or ($C_1$–$C_4$)-alkoxy, to give a compound of the formula IV

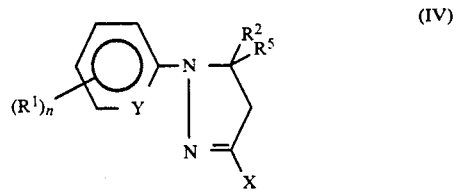

in which the substituents have said meanings, and its subsequent aromatization to give the compound I, which comprises carrying out the reaction of the compound II with the compound III to give the compound IV in a 2-phase system (aqueous/organic) in the presence of an inorganic base and then aromatizing the compound IV formed without prior isolation under acidic conditions in a 2-phase system (aqueous/organic) to give the compound of the formula I.

Alkyl is straight-chain or branched alkyl. If X=

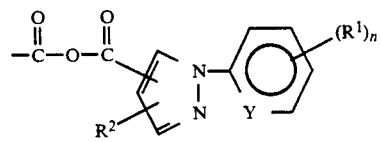

two identical radicals of a compound of the formula I are linked to one another.

Halogen is preferably chlorine or bromine, and alkali metal is preferably Li, Na, K and alkaline earth metal, in particular Ca. The heterocyclic ring formed from the two radicals $R^4$ together with the nitrogen atom is preferably pyrrolidine, morpholine, 1,2,4-triazole or piperidine.

Preferred compounds of the formula I are those in which Y is CH, $R^1$ is halogen, $R^2$ is ($C_1$–$C_6$)-alkyl, X is $COOR^3$, $R^3$ is H or ($C_1$–$C_6$)-alkyl and n=1 or 2.

Additionally preferred compounds of the formula I are those in which Y is CH, $R^1$ is Cl or Br, $R^2$ is ($C_1$–$C_4$)-alkyl, X is $COOR^3$, $R^3$ is ($C_1$–$C_4$)-alkyl and n=2, in particular the compound ethyl 1 ᴛᴍ (2,4-dichlorophenyl)-5-isopropylpyrazole-3-carboxylate.

The compounds of the formula I are known. They are used as substances which effectively reduce the phytotoxic side effects of herbicides (safeners; EP-A 333,131). Processes for their preparation are described in HU Patent 153,762 and EP-A 333,131. The preparation of the compounds of the formula IV starting from compounds of the formulae II and III and their subsequent aromatization to the target compounds I is treated in particular in German Patent Application P 39 23 649.8. In this case, the reaction is not carried out in a heterogeneous 2-phase mixture (aqueous/organic) and the two partial reactions are carried out separately, i.e. the pyrazoline IV formed is isolated before its aromatization. The base, preferably an organic base, necessary for the formation of the compound IV is added to the pure organic reaction mixture. The second partial reaction (aromatization under acidic conditions) is also carried out in an organic reaction medium without addition of water and with the aid of an organic acid. The yield of the desired final products thus obtained is about 30% over both steps, after which additional purification operations become necessary in order to separate the compounds I from the by-products formed. These by-products additionally have to be disposed of. The process described is therefore only suitable to a limited extent for carrying out a process on the industrial scale from ecological and economic points of view.

The process according to the invention, in which the pyrazolecarboxylic acid derivatives I are obtained in yields of >90% of theory and in such high purities (>95 these products can be used further without additional purification operations, avoids all of these disadvantages outlined. As isolation of the intermediates IV does not take place, the process is particularly easy to operate from the process engineering point of view. It can be carried out batchwise or continuously.

The first partial step of the reaction (formation of the pyrazoline IV) is carried out by adding an inorganic base such as, for example, alkali metal or alkaline earth metal hydroxides, carbonates or hydrogencarbonates, in particular $Na_2CO_3$, $NaHCO_3$, $K_2CO_3$ or $KHCO_3$, in the form of their aqueous solutions to the mixture of the starting compounds II and III. The cycloaddition occurring takes place in the heterogeneous 2-phase system (liquid/liquid). In this reaction, the compounds II and III form the organic phase and the solution of the inorganic base forms the aqueous polar phase. This reaction can carried out in a 2-phase system with or without additional organic solvent. Suitable organic solvents are, for example, toluene, xylene or other water-immiscible substances.

The reaction temperatures are 20°–150° C., in particular 40°–100° C., and the pH of the aqueous basic solution is between 7 and 10. The enol ethers of the formula III can be employed in equimolar amounts or in a relatively large excess (for example a 3-times excess) and, if desired, are recycled by distillation after completion of the reaction.

The positive result of this first partial step is to be judged as all the more surprising, as cycloadditions of this type in a 2-phase system (liquid/liquid) have not previously been described (for example A. S. Shawali and C. Parkányi, J. Heterocyclic Chem. 17, 833 (1980)). Addition of water during these cycloadditions should rather promote the formation of dimerization products (T. Shimizu et al., J. Org. Chem. 1985. 50, 904–907).

The addition of a phase transfer catalyst for the formation of the pyrazoline IV can be dispensed with in the process according to the invention. Under certain circumstances, however, the use of such a catalyst can be expedient. The catalysts are then the phase transfer catalysts customarily used.

The second partial reaction, the aromatization of the compounds of the formula IV to give the products I, is also carried out in a heterogeneous 2-phase mixture. For this reaction, the aqueous alkaline phase is either rendered acidic (pH values of 0–5, preferably 0–3) using acids (preferably inorganic acids, such as, for example hydrochloric or sulfuric acid), or the alkaline phase is separated off and replaced by an acidic aqueous phase. The aromatization to give the products I as a rule proceeds at the reflux temperature of the reaction mixture. This is between 20° and 200° C., in particular 15°–150° C.

The ratio of aqueous to organic phase can vary within wide limits.

A further advantage of the process according to the invention lies in the easy accessibility of the products after completion of the reaction, as these crystallize out of the 2-phase mixture on cooling with a purity above 95%. Depending on the structure of the compounds I it is expedient and frequently even advantageous to add a water-miscible solvent, such as, for example, alcohols, after completion of the reaction in order to achieve a complete, homogeneous crystallization.

The compounds of the formula (II) are known in some cases or can be synthesized by customary methods (EP-A 174,562). They can be obtained, for example, from the corresponding anilines by diazotizing and coupling with the appropriate 2-chloroacetic acid esters. The compounds of the formula (III) are also accessible by customary methods, for example by cleavage of alcohol from the corresponding ketals.

The following examples serve to illustrate the invention.

EXAMPLE 1

Ethyl 1-(2,4-dichlorophenyl)-5-isopropylpyrazole-3-carboxylate 1550 g of ethyl 2-chloroglyoxalate 2,4-dichlorophenylhydrazone are dissolved in 1000 g of 2-methoxy-3-methylbut-1-ene and a total of 600 g of potassium hydrogen-carbonate in 500 ml of water is added continuously at 70°–80° C. such that a pH of about 8–8.5 is always maintained. After a total reaction time of 4 hours, the excess enol ether (465 g) is distilled off and the reaction mixture is adjusted to a pH of 0.5 using 190 ml of hydrochloric acid. After heating to reflux for 1 hour, the mixture is cooled to room temperature and the precipitated crystallizate is filtered off with suction.

1701 g of product having a purity of 95.4% are obtained, which corresponds to a yield of 95.0% of theory. The melting point is 95°–96° C.

EXAMPLE 2

30 Ethyl 1-(2,4-dichlorophenyl)-5-isopropylpyrazole-3-carboxylate 1550 g of ethyl 2-chloroglyoxalate 2,4-dichlorophenylhydrazone are dissolved in 600 g of 2-ethoxy-3-methylbut-1-ene and 325 g of sodium carbonate, dissolved in 300 ml of water, are added such that a pH of greater than 8.0 is always maintained. After a reaction time of 4 hours (60°–80° C.), the aqueous phase is separated off and 200 ml of hydrochloric acid (pH~1) are added to the organic phase and the mixture is heated to reflux for 1 hour. After cooling to 70° C., the organic phase is separated off and crystallized using methanol/water. 1694 g of product having a purity of 96.3% are obtained, which corresponds to a yield of 94.7% of theory. The melting point is 95°–96° C.

The examples of Table I can be prepared analogously.

TABLE I

Pyrazoles I

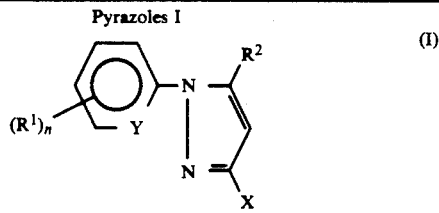

| Ex. No. | X | $(R^1)_n$ | $R^2$ | Y | Yield |
|---|---|---|---|---|---|
| 3 | $CO_2C_2H_5$ | 2.4-$Cl_2$ | $C_2H_5$ | CH | 93.2% |
| 4 | $CO_2CH_3$ | 2.4-$Cl_2$ | $CH(CH_3)_2$ | CH | 92.7% |
| 5 | $CO_2(CH_2)_2OCH_3$ | 2.4-$Cl_2$ | $CH(CH_3)_2$ | CH | 94.4% |
| 6 | $CO_2C_2H_5$ | 2.4-$Cl_2$ | $C_2H_3$ | CH | 95.1% |

TABLE I-continued

Pyrazoles I (I)

| Ex. No. | X | $(R^1)_n$ | $R^2$ | Y | Yield |
|---|---|---|---|---|---|
| 7 | $CO_2C_2H_5$ | 2.4-$Cl_2$ | $-C\equiv CH$ | CH | 91.2% |
| 8 | $CO_2C_2H_5$ | 2.4-$CF_3$—Cl | $CH(CH_3)_2$ | CH | 93.1% |
| 9 | $CO_2C_2H_5$ | 2.4-$Cl_2$ | $C_4H_9$ | CH | 92.3% |

I claim:

1. A process for the preparation of a pyrazolecarboxylic acid derivative of the formula I (I)

in which

Y is C—H or N, $R^1$ is independently of one another $(C_1-C_4)$-alkyl, $(C_1-C_4)$-haloalkyl, $(C_1-C_4)$-alkoxy, $(C_1-C_4)$-haloalkoxy or halogen, $R^2$ is $(C_1-C_{12})$-alkyl, $(C_3-C_7)$-cycloalkyl, $(C_2-C_6)$-alkenyl or $(C_2-C_4)$-alkynyl, X is $COOR^3$, $CON(R^4)_2$, $COSR^3$, CN or $R^3$ is an alkali metal or alkaline earth metal, hydrogen, $(C_1-C_{10})$-alkyl, $(C_3-C_{20})$-alkenyl, $(C_3-C_{10})$-alkynyl, $(C_3-C_7)$-cycloalkyl, phenyl-$(C_1-C_4)$-alkyl, where phenyl can be substituted by halogen, tris-$(C_1-C_4)$-alkylsilyl-$(C_1-C_4)$-alkyl or $(C_1-C_4)$-alkoxy-$(C_1-C_4)$-alkyl, $R^4$ independently of one another is H, $(C_1-C_{10})$-alkyl, $(C_3-C_7)$-cycloalkyl which can be substituted, or 2 radicals $R^4$, together with the N-atom linking them, form a 4- to 7-membered heterocyclic ring and n 1 is to 3, by reaction of a compound of the formula II (II)

in which $R^1$, X, Y and n have the abovementioned meanings and

Z is chlorine or bromine, with an enol ether of the formula III (III)

in which $R^2$ has the abovementioned meaning and $R^5$ is $(C_1-C_4)$-alkoxy, to give a compound of the formula IV (IV)

in which the substituents have said meanings, and its subsequent aromatization to give the compound I, which comprises carrying out the reaction of the compound II with the compound III to give the compound IV in a 2-phase system (aqueous/organic) in the presence of an inorganic base and then aromatizing the compound IV formed without prior isolation under acidic conditions in a 2-phase system (aqueous/organic) to give the compound of the formula I.

2. The process as claimed in claim 1, wherein, in formula I, Y is CH, $R^1$ is Cl or Br, $R^2$ is $(C_1-C_4)$-alkyl, X is $COOR^3$, $R^3$ is $(C_1-C_4)$-alkyl and n=2.

3. The process as claimed in claim 1 or 2, wherein the compound of the formula I is ethyl 1-(2,4-dichlorophenyl)-5-isopropylpyrazole-3-carboxylate.

4. The process as claimed in claim 1, wherein the reaction of the compound II with the compound III to give the intermediate IV is carried out at temperatures of 40°-100° C. and at pH values of 7-10.

5. The process as claimed in claim 1, wherein an aqueous solution of $Na_2CO_3$, $NaHCO_3$, $K_2CO_3$ or $KHCO_3$ is used in the reaction of the compound II with the compound III to give the intermediate IV.

6. The process as claimed in claim 1, wherein the reaction of the intermediate IV to give the compound I is carried out at pH values of 0-3 and at the reflux temperature of the reaction mixture.

* * * * *